(12) United States Patent
Akitomo

(10) Patent No.: US 10,130,796 B2
(45) Date of Patent: Nov. 20, 2018

(54) GUIDE WIRE AND METHOD FOR MANUFACTURING A GUIDE WIRE

(71) Applicant: TERUMO KABUSHIKI KAISHA, Shibuya-ku, Tokyo (JP)

(72) Inventor: Dai Akitomo, Fujinomiya (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 0 days.

(21) Appl. No.: 15/363,363

(22) Filed: Nov. 29, 2016

(65) Prior Publication Data

US 2017/0072170 A1    Mar. 16, 2017

Related U.S. Application Data

(63) Continuation of application No. PCT/JP2015/076513, filed on Sep. 17, 2015.

(30) Foreign Application Priority Data

Sep. 25, 2014  (JP) ................. 2014-194940

(51) Int. Cl.
| | |
|---|---|
| *A61M 25/09* | (2006.01) |
| *B23K 31/02* | (2006.01) |
| *C22C 19/00* | (2006.01) |
| *C22C 19/03* | (2006.01) |
| *B23K 101/32* | (2006.01) |

(52) U.S. Cl.
CPC ............. *A61M 25/09* (2013.01); *B23K 31/02* (2013.01); *C22C 19/007* (2013.01); *C22C 19/03* (2013.01); *A61M 2025/0915* (2013.01); *A61M 2025/09075* (2013.01); *A61M 2025/09083* (2013.01); *A61M 2025/09108* (2013.01); *A61M 2025/09141* (2013.01); *B23K 2201/32* (2013.01)

(58) Field of Classification Search
CPC ........ A61M 25/09; A61M 2025/09175; A61M 2025/09083
USPC ....................................................... 600/585
See application file for complete search history.

(56) References Cited

U.S. PATENT DOCUMENTS

| | | | |
|---|---|---|---|
| 7,785,274 B2 | 8/2010 | Mishima et al. | |
| 2004/0030265 A1* | 2/2004 | Murayama | A61M 25/09 600/585 |
| 2009/0157050 A1* | 6/2009 | Fujimagari | A61M 25/09033 604/528 |

FOREIGN PATENT DOCUMENTS

JP            201476132 A  *  5/2014

\* cited by examiner

*Primary Examiner* — Daniel Cerioni
(74) *Attorney, Agent, or Firm* — Buchanan Ingersoll & Rooney PC

(57) ABSTRACT

A guide wire includes an elongated core wire possessing a distal portion at which is located a reshaping portion that is configured to be reshaped. The reshaping portion includes a first material portion made of a first material and a second material portion which is made of a second material different than the first material. The first material portion is joined to the second material portion at a joint surface which extends in the longitudinal direction of the core wire.

23 Claims, 6 Drawing Sheets

GUIDE WIRE AND METHOD FOR MANUFACTURING A GUIDE WIRE

CROSS-REFERENCES TO RELATED APPLICATIONS

This application is a continuation of International Application No. PCT/JP2015/076513 filed on Sep. 17, 2015, and claims priority to Japanese Patent Application No. 2014-194940 filed on Sep. 25, 2014, the entire content of both of which is incorporated herein by reference.

TECHNICAL FIELD

The present invention relates to a guide wire and a method for manufacturing the guide wire.

BACKGROUND DISCUSSION

A guide wire is used for guiding a catheter to a treatment site where it is difficult to perform a surgical operation. For example, a guide wire may be used in percutaneous transluminal coronary angioplasty (PTCA) or treatment which is aimed to be less invasive to the human body, or used in tests such as cardioangiography. The guide wire used in PTCA is inserted into the vicinity of a stenosed site of a blood vessel (i.e., the target site) together with a balloon catheter in a state in which a distal end of the guide wire protrudes from a distal end of the balloon catheter. The distal portion of the balloon catheter is thus guided by the guide wire to the vicinity of the stenosed site of a blood vessel.

Blood vessels are complicatedly curved. Therefore, a guide wire used when inserting a balloon catheter into a blood vessel requires suitable flexibility and resilience with respect to bending, pushability and torquability (which are collectively called "operability") for transmitting an operation at a proximal portion to a distal side of the guide wire. A guide wire also requires suitable tensile strength, kink resistance (bending resistance), and the like. A configuration for obtaining suitable flexibility and resilience includes a structure of a double metal coil (being flexible with respect to bending) around a thin distal core of a guide wire and a structure in which a super elastic wire such as Ni—Ti wire is used in a core of a guide wire. An example is disclosed in U.S. Pat. No. 7,785,274. In addition, a reinforcing material that is separately provided at a distal portion of a core is known to improve torquability (i.e., ability to transmit torque to a distal portion of the guide wire so that the guide wire can be maneuvered such as being rotated and/or twisted).

When the guide wire is used for PTCA, pushability is decreased if the distal portion of the core is thin, so that the guide wire may be used as safely as possible while avoiding penetration of a wall of a blood vessel. However, a transverse cross-sectional area should not be excessively reduced in order to maintain sufficient tensile strength of the guide wire so as to avoid breakage. Furthermore, in some cases, reshaping of the distal portion of the core is performed during PTCA. For example, the distal portion of the core may be pressed into a flat plate shape in order to easily perform this reshaping. Accordingly, the pushability of the distal end decreases, thereby improving safety. However, torquability significantly decreases. In addition, although the torquability may be improved when the reinforcing material is separately provided, it is difficult to perform the reshaping of the distal portion of the core.

Therefore, in the guide wire in the related art, it is difficult to achieve coexistence of improvement in easiness of the reshaping at the distal portion and torquability up to the distal portion while maintaining safe pushability and tensile strength.

SUMMARY

This application describes a guide wire that can be relatively easily reshaped at a distal portion of the guide wire and which is excellent in torquability up to the distal portion. The present application also describes a method for manufacturing the guide wire.

This application includes the following aspects numbered (1) to (13).

(1) A guide wire includes a core wire having an elongated shape and having a reshaping portion, which can be reshaped, at a distal portion, in which the reshaping portion has at least a first material portion made of a first material, and a second material portion which is made of a second material different from the first material and is joined to the first material portion, and in which the joint surface between the first material portion and the second material portion follows a longitudinal direction of the core wire.

(2) The guide wire according to the above-described (1), in which a transverse cross sectional shape of the reshaping portion is a circular shape or an elliptical shape.

(3) The guide wire according to the above-described (2), in which the joint surface is shifted from a center of the circular shape or the elliptical shape.

(4) The guide wire according to the above-described (2), in which the transverse cross sectional shapes of the first material portion and the second material portion respectively are fan shapes, and in which a central angle of the first material portion and a central angle of the second material portion are different from each other.

(5) The guide wire according to the above-described (2), in which the reshaping portion has two material portions on one side of the first material portion and the second material portion and one material portion on the other side, and the material portion in the other side is disposed between the two material portions in the one side.

(6) The guide wire according to any one of the above-described (1) to (5), in which the core wire has a main body portion which is positioned on a proximal side of the reshaping portion is thicker than that of the reshaping portion, and is made of the first material or the second material.

(7) The guide wire according to the above-described (6), in which one of the first material portion and the second material portion which is made of the same constituent material as that of the main body portion is formed integrally with the main body portion.

(8) The guide wire according to the above-described (7), in which one of the first material portion and the second material portion which is made of the same constituent material as that of the main body portion has a large cross-sectional area ratio in the cross-section of the reshaping portion.

(9) The guide wire according to any one of the above-described (1) to (8), in which one of the first material and the second material is stainless steel and the other is Ni—Ti based alloy.

(10) The guide wire according to any one of the above-described (1) to (9), in which the reshaping portion has a third material portion which is made of a third material different from the first material and the second material and is joined to the first material portion and the second material portion between the first material portion and the second material portion.

(11) The guide wire according to the above-described (10), in which one of the first material and the second material is stainless steel and the other is Ni—Ti based alloy, and the third material is β-Ti.

(12) A method for manufacturing a guide wire which includes a core wire having an elongated shape and having a reshaping portion, which can be reshaped, at a distal portion, in which the reshaping portion has at least a first material portion made of a first material, and a second material portion which is made of a second material different from the first material and is joined to the first material portion, and in which, when performing joining of the first material portion and the second material portion, the joining is performed such that the joint surface follows a longitudinal direction of the core wire.

(13) The method for manufacturing a guide wire according to the above-described (12), in which at least one of pressurizing and heating is used for the joining.

In another aspect of the disclosure here, a guide wire includes a main body extending in a longitudinal direction and a tapered portion. The proximal end of the tapered portion is connected to the distal-most end of the main body. The guide wire also includes a first extension portion. The proximal end of the first extension portion is directly connected to the distal end of the tapered portion. The main body, the tapered portion, and the first extension portion are integrally formed at one time as a unitary structure from a first material. The guide wire includes a second extension portion made from a second material different from the first material. The second extension portion is joined to the first extension portion at a joint surface extending in the longitudinal direction. The first extension portion and the second extension portion collectively define a reshaping portion of the guide wire. The first material forming part of the outer surface of the reshaping portion and the second material forming another part of the outer surface of the reshaping portion.

In addition, the joint surface of the guide wire preferably passes through the center of the circular shape or the elliptical shape.

It is also preferable that the transverse cross sectional shapes of the first material portion and the second material portion respectively are fan shapes and a central angle of the first material portion and a central angle of the second material portion are the same as each other.

According to the guide wire of this application, the reshaping portion is constructed from different types of materials and has a first material portion and a second material portion which are joined to each other, and the joint surface of the first and second material portions follows a longitudinal direction of a core wire. Accordingly, it is possible to easily perform reshaping of a distal portion (reshaping portion) of a guide wire and to reliably transmit torque to the distal portion (i.e., the guide wire is excellent in torquability).

DETAILED DESCRIPTION

Hereinafter, a guide wire and a method for manufacturing the guide wire will be described in detail based on the embodiments shown in the accompanying drawings.

First Embodiment

Figure 1:
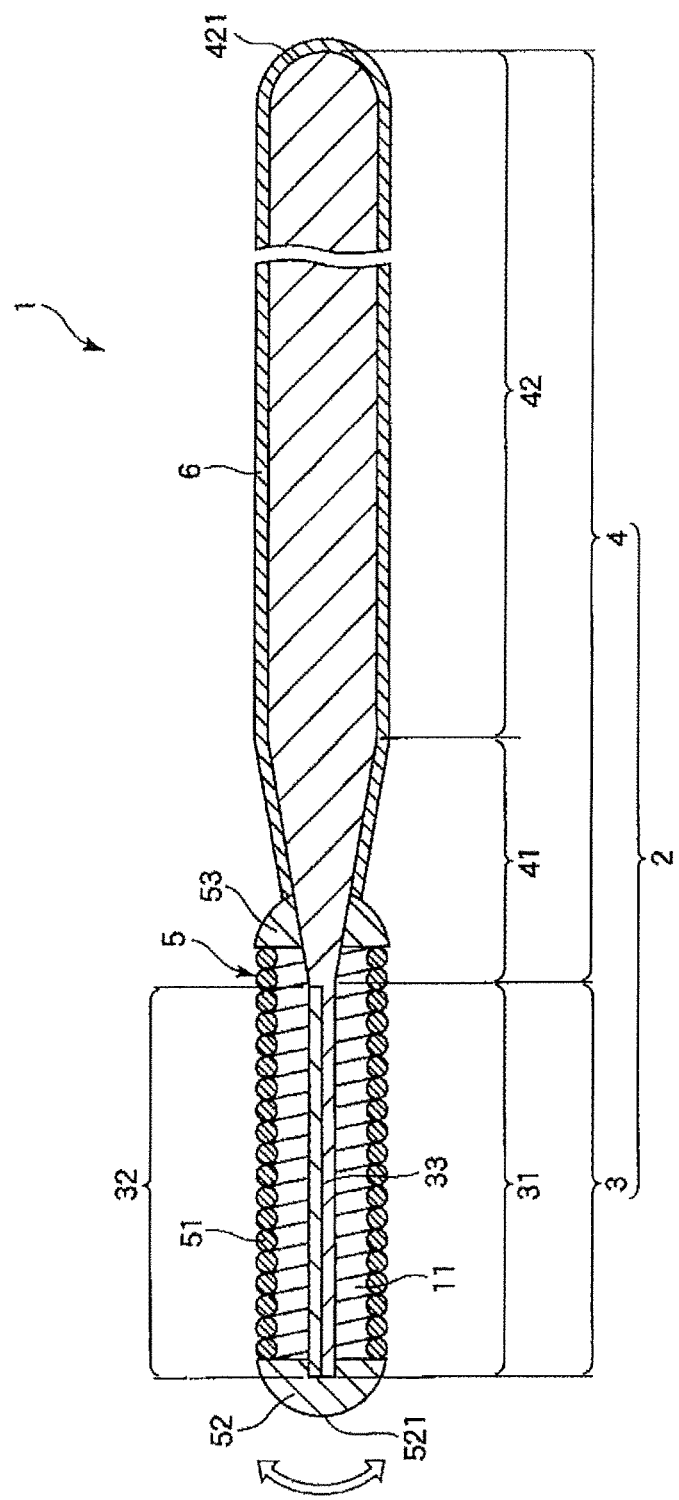
FIG. 1 is a longitudinal sectional view showing a first embodiment of a guide wire.
Figure 2A:
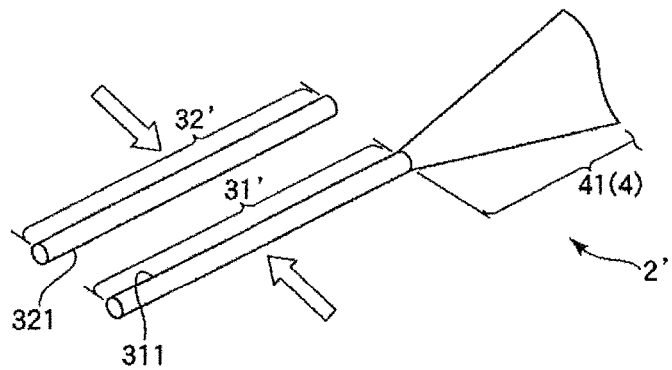
FIGS. 2(a) and 2(b) are perspective views showing a process of manufacturing a core wire (reshaping portion) provided in the guide wire shown in FIG. 1.
Figure 2B:
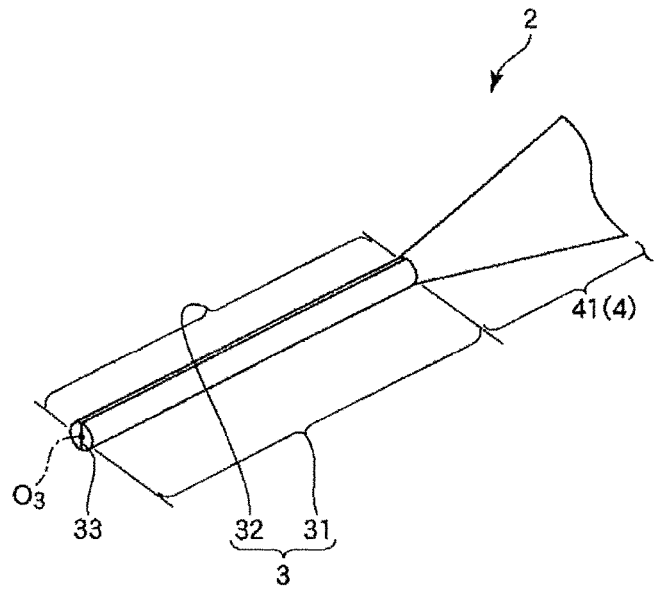
Figure 3A:
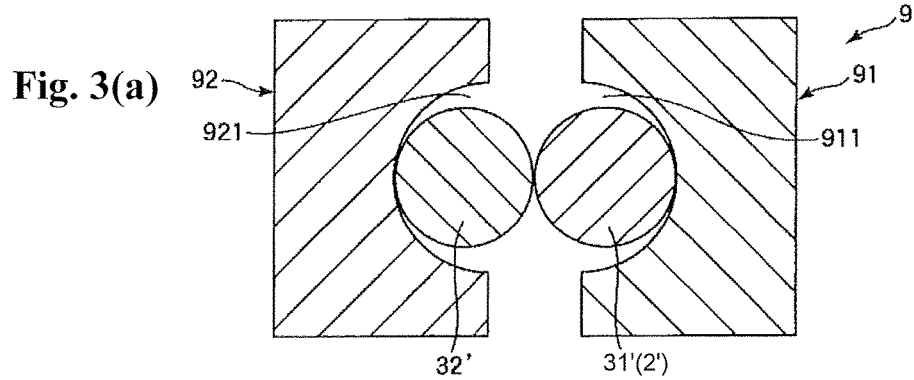
FIGS. 3(a)-3(c) are cross sectional views showing a process of manufacturing the core wire (reshaping portion) provided in the guide wire shown in FIG. 1.
Figure 3B:
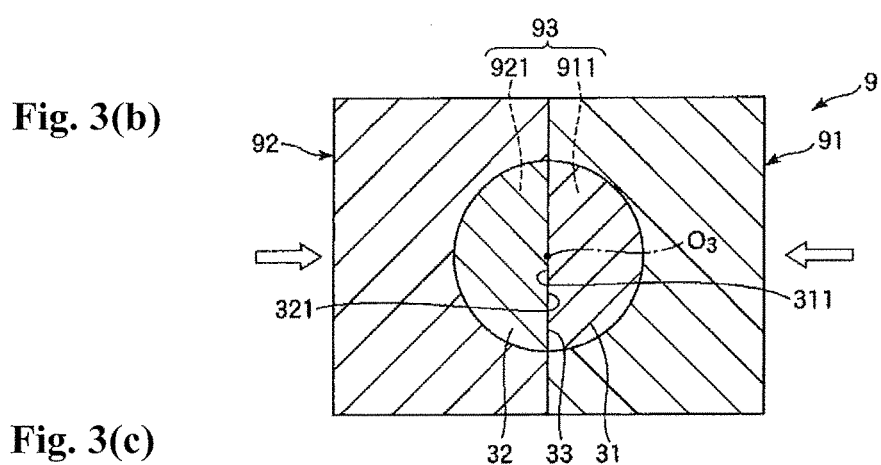
Figure 3C:
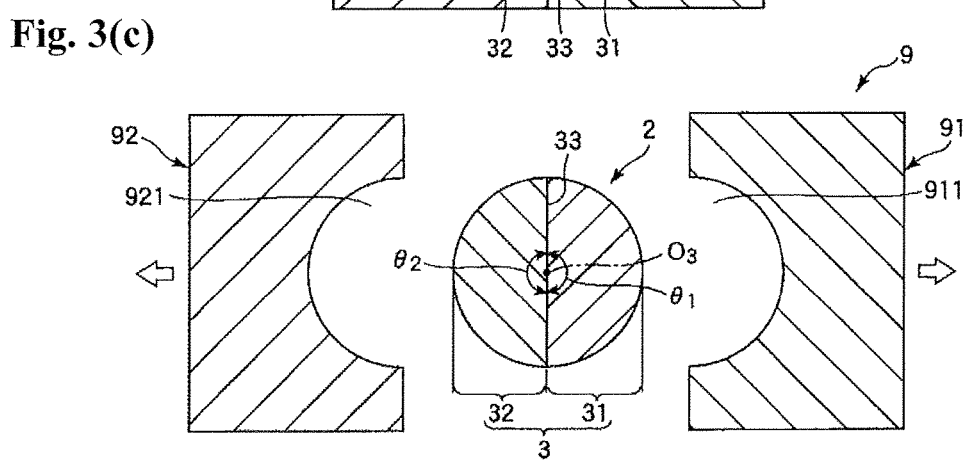

FIG. 1 is a longitudinal sectional view showing a first embodiment of the guide wire disclosed here. FIGS. 2(a)-2(b) are perspective views showing a process of manufacturing a core wire (reshaping portion) provided in the guide wire shown in FIG. 1. FIGS. 3(a)-3(c) are cross sectional view showing a process of manufacturing the core wire (reshaping portion) provided in the guide wire shown in FIG. 1. Note that, in the below description, a right side and a left side in FIGS. 1, 2(a), 2(b), 4(a) and 4(b) are respectively referred to as the "proximal end" or "proximal side" and the "distal end" or "distal side", respectively. The guide wire is schematically illustrated in FIGS. 1, 2(a), 2(b), 4(a) and 4(b) by shortening the longitudinal direction of the guide wire and exaggerating the thickness direction of the guide wire for easy observation (i.e., to more clearly illustrate the features of the guide wire). The proportion of the longitudinal direction to the thickness direction is significantly different from reality.

The guide wire 1 shown in FIG. 1 is a guide wire that is insertable into a lumen of a catheter (including an endoscope) to be used in, for example, PTCA. The total length of the guide wire 1 is not particularly limited, but is preferably about 200 to 5,000 mm. This guide wire 1 includes a core wire (wire main body) 2 constituted of a single wire forming an elongated shape. The guide wire 1 also includes a spiral coil 5 provided at a distal portion (a portion on a distal side) of the core wire 2.

The core wire 2 includes a reshaping portion 3 positioned on the distal side and a main body portion 4 positioned on the proximal side of the reshaping portion 3.

The reshaping portion 3 is capable of being reshaped. For example, the reshaping portion 3 can be bent or curved in the direction of the arrow in FIG. 1 so as to be deformed into a predetermined shape. In some cases, a doctor or the like generally deforms the distal portion of the guide wire into a predetermined shape in advance (i.e., before the guide wire 1 is inserted into a living body) to make the distal portion of a catheter (or the like to be guided to the target site) correspond to a shape of a blood vessel, or to accurately and smoothly select a vascular branch and to guide the catheter, and then use the guide wire. Bending of the distal portion of the guide wire in a predetermined shape in this manner is called reshaping. It is possible to easily and reliably perform the reshaping by providing the reshaping portion 3. Operability during insertion of the guide wire 1 into a living body is thus significantly improved. Note that a marker showing a preferable bending direction of the distal portion may be provided at the distal portion of the guide wire 1.

The main body portion 4 is a portion of the guide wire 1 which is thicker and longer than the reshaping portion 3. The main body portion 4 includes a tapered portion 41 forming a tapered shape such that the outer diameter is gradually increased toward a proximal direction (i.e., the proximal end of the tapered portion 41 has a larger outer diameter than the distal end of the tapered portion 41) and a constant outer diameter portion 42 which has a constant outer diameter.

It is possible to gradually reduce the rigidity (flexural rigidity or torsional rigidity) of the core wire 2 toward a distal direction (i.e., the distal end is less rigid than the proximal end) using the tapered portion 41 located between the reshaping portion 3 and the constant outer diameter portion 42. As a result, the distal portion of the guide wire 1 exhibits favorable flexibility and properties permitting the guide wire to pass a stenosed site (e.g., maneuverability to reach and/or enter a stenosed site). The guide wire 1 can also have improved safety, followability to a blood vessel (i.e., maneuverability within or along a blood vessel) or the like, and prevent bending or the like. Note that the taper angle (a decrease rate of the outer diameter) of the tapered portion 41 may be constant along the longitudinal direction of the core wire 2, or may have a site changing along the longitudinal direction (i.e., the taper of the tapered portion 41 may be non-constant). For example, a configuration may be adapted in which a plurality of portions of which the taper angle is comparatively large and a plurality of portions of which the taper angle is comparatively small alternate.

The outer diameter of the constant outer diameter portion 42 is the same as the maximum outer diameter of the tapered portion 41. The constant outer diameter portion is a portion in which the rigidity is comparatively high (e.g., possesses higher rigidity than the distal portion of the tapered portion 41). Accordingly, pushability in the distal direction of the guide wire 1 become favorable. Note that a proximal surface 421 of the constant outer diameter portion 42 is preferably rounded as illustrated in FIG. 1.

As shown in FIG. 1, the coil 5 is disposed on the outer circumference of the reshaping portion 3 of the core wire 2 so as to cover (i.e., surround) the reshaping portion 3. This coil 5 causes the contact area of the surface of the core wire 2 with the inner wall of a catheter or the surface of a living body to decrease. Accordingly, it is possible to reduce frictional resistance. Operability of the guide wire 1 is thus improved.

The reshaping portion 3 is inserted into a central portion on the inside of the coil 5 and enters a non-contact state with the inner surface of the coil 5 (i.e., the outer surface of the reshaping portion 3 does not contact the inner surface of the coil 5). Accordingly, a gap 11 is formed between the coil 5 and the reshaping portion 3, and it is possible to decrease pushability with respect to a blood vessel.

The coil 5 is formed by winding a strand 51 along the circumferential direction of the reshaping portion 3 in a spiral shape. One strand 51 may be wound in a spiral shape, or a plurality of strands 51 may be wound in a spiral shape.

In the example shown in FIG. 1, the strands 51 of the coil 5 are densely wound such that axially adjacent strands 51 contact each other (i.e., the strands 51 exhibit a densely wound state). These strands 51 mutually (i.e., collectively) generate a pushing force (expansion force) in an axial direction of the core wire 2 in a natural state in which no external force is applied. Note that the guide wire 1 is not limited to this configuration, and there may be a so-called roughly wound portion in which the axially adjacent strands 51 of the coil 5 are separated from each other (i.e., the axially adjacent strands 51 are spaced apart from one another).

The constituent material of the strand 51 is not particularly limited, and may be either a metal material or a resin material. Examples of the metal material include stainless steel or a radiopaque material such as noble metal such as Au or Pt and alloy (for example, Pt—Ni alloy) including the noble metal. When a radiopaque material is used, the distal portion of the guide wire 1 can obtain radiopacity so that it is preferably possible to insert the guide wire into a living body while checking the position of the distal portion under X-ray fluoroscopy.

The coil 5 may be obtained by combining two or more types of materials. For example, the strands 51 on the distal side of the coil 5 can be made of a radiopaque material such as Pt—Ni alloy and/or the strands 51 on the proximal side of the coil 5 can be made of stainless steel. It is thus possible to emphasize a site (particularly, a site including the reshaping portion 3) positioned on the distaff side of the coil 5 more than a site positioned further on the proximal side under X-ray fluoroscopy. Accordingly, it is possible to more clearly visualize the position of the most distal portion (a portion in which the reshaping portion 3 exists) of the guide wire 1.

In addition, the wire diameters of the strands 51 of the coil 5 may be the same as one another over the total length of the coil 5, or the wire diameters of the strands 51 may be different from one another on the distal side and the proximal side of the coil 5. For example, the wire diameters of the strands 51 may be relatively smaller (or larger) on the distal side or distal end of the coil 5 compared to those on the proximal side or proximal end. Accordingly, it is possible to improve penetrating properties of the guide wire 1 through a lesion area at the distal portion of the coil 5 (i.e., a small diameter distal-most end of the coil 5 may more easily penetrate a lesion area).

The outer diameter of the coil 5 may be constant over the total length of the coil 5, or may be non-constant from the distal side to the proximal side of the coil 5. For example, the outer diameter of the coil 5 may become small on the distal side of the coil 5 compared to that on the proximal side. Accordingly, it is possible to improve flexibility of the guide wire 1 at the distal portion of the coil 5.

As shown in FIG. 1, the coil 5 is fixed to two portions with respect to the core wire 2. That is, the distal portion of the coil 5 is fixed to the distal end of the reshaping portion 3 through a fixation material (fixation portion) 52, and the proximal portion of the coil 5 is fixed to a midway portion of the tapered portion 41 through a fixation material (fixation portion) 53. By fixing the coil to the reshaping portion 3 and the tapered portion 41, it is possible to reliably fix the coil 5 to the core wire 2 while preventing impairment of flexibility (i.e., decreased flexibility) of the distal portion (site in which the coil 5 exists) of the guide wire 1.

It is possible to reliably fix the reshaping portion 3 to the coil 5 and to accurately maintain the shape of the reshaped reshaping portion 3 because the distal side and the proximal side of the reshaping portion 3 are respectively fixed using the fixation materials 52 and 53.

It is preferable that the fixation materials 52 and 53 are respectively formed of solder (brazing material). The fixation materials 52 and 53 may also be adhesives. The method for fixing the coil 5 to the core wire 2 is not limited to the method using the fixation materials, and may be performed through, for example, welding.

Note that a distal surface 521 of the fixation material 52 is preferably rounded in order to prevent damage to the inner wall of a body cavity such as a blood vessel.

As shown in FIG. 1, there is a resin covering layer 6 which entirely or partially covers a portion further on the proximal side than the fixation material 53 of the core wire 2. This resin covering layer 6 can be formed for various purposes. For example, in some cases, the resin covering layer improves operability of the guide wire 1 by decreasing friction (sliding resistance) of the guide wire 1 and thus enhancing sliding properties.

In order to achieve a decrease in friction (sliding resistance) of the guide wire 1, the resin covering layer 6 is preferably made of a lower friction material described below. Accordingly, sliding properties are improved by the decrease in friction resistance (sliding resistance) with an inner wall of a catheter which is used together with the guide wire 1. Operability of the guide wire 1 within the catheter thus becomes more favorable. In addition, it is possible to more reliably prevent kinking (bending) or twisting of the guide wire 1 when the guide wire 1 is moved and/or rotated within the catheter by decreasing the sliding resistance of the guide wire 1.

Examples of materials that can be used for the resin covering layer 6 to decrease friction include polyolefins such as polyethylene and polypropylene, polyvinyl chloride, polyester (PET, PBT, or the like), polyamide, polyimide, polyurethane, polystyrene, polycarbonate, a silicone resin, a fluorine resin (PTFE, ETFE, or the like), or a composite material of these materials.

Note that the resin covering layer 6 may be a single layer or may be a laminated body (for example, a body of which an inner layer is made of a more flexible material compared to an outer layer) having two or more layers.

As shown in FIG. 1, the reshaping portion 3 of the guide wire 1 is constituted of a first material portion 31 and a second material portion 32. The first material portion 31 and the second material portion 32 are made of different two kinds of materials. The reshaping portion 3 is an elongated portion/body in which the first material portion 31 and the second material portion 32 are joined to each other at a joint surface (boundary surface) 33. The joint surface 33 illustrated in FIG. 1 follows the longitudinal direction (i.e., the horizontal direction in FIG. 1) of the core wire 2.

The outer diameter of the reshaping portion 3 is the same as the minimum outer diameter of the tapered portion 41. For example, the other diameter of the reshaping portion 3 preferably is 0.05 mm to 0.2 mm and more preferably is 0.08 mm to 0.15 mm. The total length of the reshaping portion 3 is not particularly limited. For example, the total length of the reshaping portion 3 preferably is 2 mm to 100 mm and more preferably is 5 mm to 20 mm.

The material of the first material portion 31 is not particularly limited. Examples of acceptable materials to employ for the first material portion 31 include various metal materials such as stainless steel (for example, all types of SUS such as SUS304, SUS303, SUS316, SUS316L, SUS316J1, SUS316J1L, SUS405, SUS430, SUS434, SUS444, SUS429, SUS430F, and SUS302) and piano wires. Among these, stainless steel is preferable.

The material of the second material portion 32 is different from the first material, but the material of the second material portion 32 is not particularly limited. Examples of acceptable materials to employ for the second material portion 32 include super elastic alloys exhibiting super elasticity in a living body. Examples of permissible super elastic alloys include one that has a tension stress-strain curve having any shape, include ones in which a transformation point such as As, Af, Ms, and Mf can be or cannot be noticeably measured, and include all kinds of super elastic alloy which are greatly deformed (distorted) by a stress and almost return to an original shape in response to removal of the stress. Examples of preferred compositions of super elastic alloy include Ni—Ti based alloy such as Ni—Ti alloy with 49 to 52 atom % Ni, Cu—Zn alloy with 38.5 to 41.5 wt % Zn, Cu—Zn—X alloy with 1 to 10 wt % X (X is at least one of Be, Si, Sn, Al, and Ga), and Ni—Al alloy with 36 to 38 atom % Al. Among these, the above-described Ni—Ti based alloy is particularly preferable. Note that super elastic alloy represented by Ni—Ti based alloy is excellent in adhesiveness with the resin covering layer 6.

The main body portion 4 is also made of the first material which is the same as the constituent material of the first material portion 31. In the present embodiment, the main body portion 4 and the first material portion 31 are integrally formed at the same time as a unitary structure (refer to FIGS. 2(a)-2(b)).

Accordingly, the manufacturing of the core wire 2 (guide wire 1) is facilitated.

Stainless steel constituting the first material portion 31 has higher strength and rigidity compared to those of super elastic alloy. Accordingly, the first material portion 31 has a function of transmitting torque or another push-in force from the main body portion 4 of the core wire 2 to the distal end of the guide wire 1 in the reshaping portion 3 (i.e., a force in the distal direction).

Ni—Ti based alloy constituting the second material portion 32 has sufficient flexibility and has resilience. Therefore, bending tendency hardly occurs. In the reshaping portion 3, reshaping is easily performed by these second material portion 32 and first material portion 31 together. The shape of the reshaping portion 3 can thus be reliably maintained.

This configuration of the reshaping portion 3 of the guide wire 1 makes it is relatively easy to perform reshaping at the distal portion the guide wire 1 and provides excellent torquability up to the distal portion of the guide wire 1. The reshaping portion 3 can also obtain sufficient flexibility and resilience with respect to bending because the second material portion 32 is provided in the guide wire 1. The flexibility and resilience of the guide wire 1 allows it to obtain excellent operability due to improved followability with respect to blood vessels or the like which are complicatedly curved and bent. In addition, even if the reshaping portion 3 repeats deformation of curving and bending, the reshaping portion does not tend to bend due to the resilience provided in the second material portion 32. Therefore it is possible to prevent deterioration in operability due to bending tendency occurring in the reshaping portion 3 when using the guide wire 1.

As shown in FIGS. 2(b) and 3(c), the transverse cross sectional shape of the reshaping portion 3 is a circular shape, and the joint surface 33 passes through (includes) the center $O_3$ of the cross sectional shape of the reshaping portion 3. Accordingly, the transverse cross sectional shape of the first material portion 31 forms a semi-circular shape, that is, a central angle $\theta_1$ forms a fan shape at 180°. The transverse cross sectional shape of the second material portion 32 also forms a semi-circular shape similarly to the transverse cross sectional shape of the first material portion 31, that is, a central angle $\theta_2$ forms a fan shape at 180°. In other words, the first material portion 31 and the second material portion 32 each form one-half of the cylindrical shape of the reshaping portion 3.

The first material portion 31 and the second material portion 32 in the reshaping portion 3 of the present embodiment are thus the same as each other (i.e., equal in volume/size to one another). Accordingly, the joint surface 33 of the first material portion 31 and the second material portion 32 appears at a position symmetrical in the circumferential direction. Therefore, there is an advantage in that it is easy to perform shaping during a procedure.

Next, a method for manufacturing the core wire 2 (guide wire 1) by joining the first material portion 31 and the second material portion 32 to each other will be described in reference to FIGS. 2(a)-3(c).

As shown in FIGS. 3(a)-3(c), a mold 9 which includes a first mold 91 and a second mold 92 enabling a mold closing action (as illustrated in FIG. 3(b)) and a mold opening action (as illustrated in FIGS. 3(a) and 3(c)) is used in this manufacturing method.

The first mold 91 and the second mold 92 form a cavity 93 which molds the reshaping portion 3 in the mold closing state (i.e., when the mold 9 is closed). That is, the first mold 91 has a space 911 forming a semi-cylindrical shape and the second mold 92 also has a space 921 forming a semi-cylindrical shape. The cavity 93 which molds the reshaping portion 3 can be formed/defined by these spaces 911 and 921 communicating with each other in the mold closing state. The cavity 93 can also extend to encompass a portion of the tapered portion 41 so that there is a smooth transition from the reshaping portion 3 to the taper portion 41.

When manufacturing the core wire 2, first, a preform 2' having the main body portion 4 is prepared as shown in FIG. 2(a). A first portion to be formed (a portion that will form the first material portion) 31' for forming the first material portion 31 (i.e., the material that becomes the first material portion 31 after molding) is integrally protrusively formed at a distal end of the tapered portion 41 of this preform 2' (i.e., the first portion to be formed 31' that becomes the first material portion 31 is integrally formed at the same time as the tapered portion 41 so that the tapered portion 41 and the first portion to be formed 31' constitute a unitary structure). The transverse cross sectional shape of the first portion to be formed 31' is a circular shape in the present embodiment, and the first portion to be formed 31' is thinner than the first material portion 31.

In addition, a second portion to be formed (a portion that will form the second material portion) 32' is also prepared as a preform for forming the second material portion 32 (i.e., a portion that will become the second material portion 32 after molding) in addition to the preform 2'. The transverse cross sectional shape of the second portion to be formed 32' is a circular shape in the present embodiment and the second portion to be formed 32' is thinner than the second material portion 32.

Next, as shown in FIG. 3(a), the first portion to be formed 31' and the second portion to be formed 32' are disposed between the first mold 91 and the second mold 92 in a mold opening state. The first portion to be formed 31' is positioned in the space 911 of the first mold 91 and the second portion to be formed 32' is positioned in the space 921 of the second mold 92.

Next, at least one of pressurizing and heating is carried out while performing mold closing as shown in FIG. 3(b). Specifically, the first portion to be formed 31' and the second portion to be formed 32' are fused through joining methods such as friction pressure welding or upset welding, and a combination of joining methods, to reliably join side surfaces 311 and 321 to one another.

Next, the mold enters the mold opening state again (i.e., the mold is opened) as shown in FIG. 3(c). Accordingly, as shown in FIGS. 2(b) and 3(c), the first material portion 31 and the second material portion 32 are joined to each other. The core wire 2 thus has a joint surface 33 that joins the first material portion 31 and the second material portion 32 to define the reshaping portion 3. The joint surface 33 extends along the longitudinal direction of the core wire 2. This reshaping portion 3 becomes a portion in which it is easy to perform reshaping and which is excellent in torquability as described above.

Second Embodiment

Figure 4A:
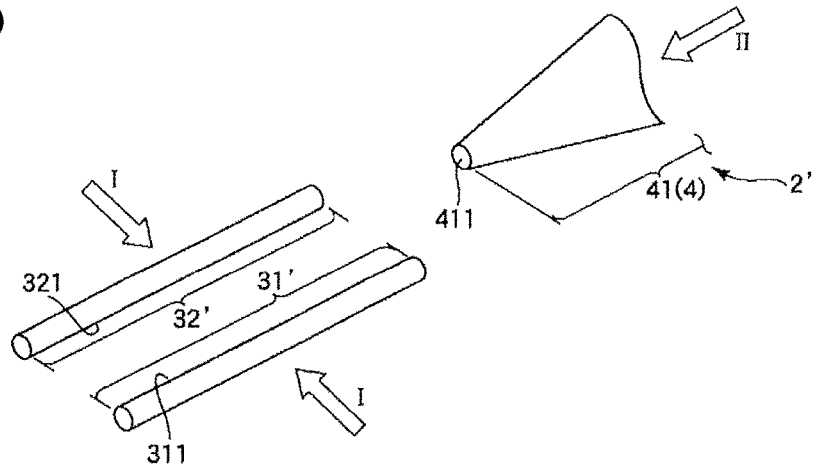
FIGS. 4(a) and 4(b) are perspective views showing a process of manufacturing a core wire (reshaping portion) provided in a guide wire (second embodiment).
Figure 4B:
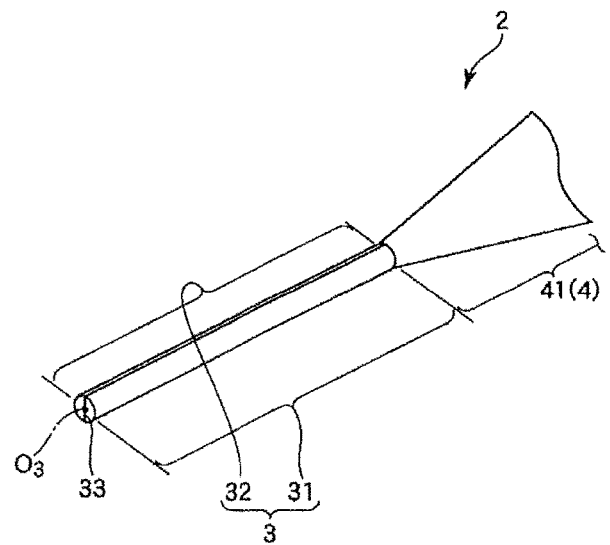

FIGS. 4(a) and 4(b) are perspective views showing a process of manufacturing a core wire (reshaping portion) provided in a second embodiment of the guide wire.

Hereinafter, the second embodiment of the guide wire and a method for manufacturing the guide wire will be described while referring to FIGS. 4(a)-4(b). However, the description will mainly focus on differences between the second embodiment and the above-described embodiment, and the description of the same features will not be repeated.

The second embodiment is the same as the first embodiment except that the process of manufacturing the core wire is different than in the first embodiment. As shown in FIGS. 4(a)-4(b), the first portion to be formed 31' of the second embodiment is a preform formed separately from the preform 2' until the core wire 2 is obtained.

As shown in FIG. 4(a), the first portion to be formed 31' and the second portion to be formed 32' are first joined to each other (arrow "I") and end surfaces of the joint bodies are subsequently joined to a distal surface 411 of the preform 2' (arrow "II"). The mold 9 in the above-described embodiment is used for the joining in the arrow "I". The joining of the end surfaces of the joint bodies to the distal surface 411 as identified by the arrow "II", for example, is performed by butt resistance welding such as friction stir welding (FSW), friction pressure welding, spot welding using a laser, or upset welding. The core wire 2 shown in FIG. 4(b) is obtained through such joining.

Third Embodiment

Figure 5:
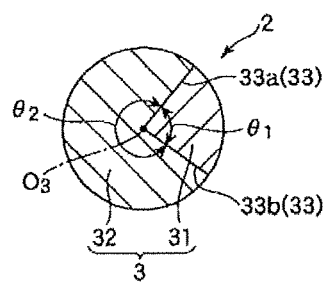
FIG. 5 is a transverse cross sectional view showing a reshaping portion in a guide wire (third embodiment).

FIG. 5 is a transverse cross sectional view showing a reshaping portion in a third embodiment of the guide wire.

Hereinafter, the third embodiment of the guide wire and a method for manufacturing the guide wire will be described while referring to this drawing. However, the description will focus on differences between the third embodiment and the above-described embodiments, and the description of the same features will not be repeated.

The third embodiment is the same as the first embodiment except that the configuration of the first material portion and the second material portion constituting the reshaping portion is different than in the first embodiment.

In the embodiment shown in FIG. 5, the transverse cross sectional shape of the first material portion 31 and the transverse cross sectional shape of the second material portion 32 are fan shapes of which central angles are different from each other. In the configuration shown in FIG. 5, a central angle $\theta_1$ of the first material portion 31 is smaller than a central angle $\theta_2$ of the second material portion 32. Accordingly, in the reshaping portion 3, the occupancy (i.e., the volume) of the first material portion 31 becomes smaller than that of the second material portion 32. Such a configuration is effective when, for example, torque performance in the reshaping portion 3 needs to be improved.

There are two joint surfaces 33 (joint surfaces 33a and 33b) in the third embodiment, and all of the joint surfaces 33a and 33b pass through a center $O_3$ and follow (i.e., extend in) a longitudinal direction of the core wire 2.

In addition, the magnitude relation between the central angle $\theta_1$ and the central angle $\theta_2$ is $\theta_1 < \theta_2$ in the third embodiment illustrated in FIG. 5. However, the magnitude relation is not limited to this configuration and may be $\theta_1 > \theta_2$, such that the occupancy (i.e., volume) of the first material portion 31 is larger than that of the second material portion 32 in the reshaping portion 3. Such a configuration is effective when, for example, shape maintaining properties in the reshaping portion 3 need to be preferentially improved.

Fourth Embodiment

Figure 6:
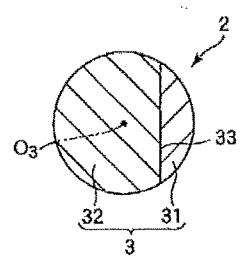
FIG. 6 is a transverse cross sectional view showing a reshaping portion in a guide wire (fourth embodiment).

FIG. 6 is a transverse cross sectional view showing a reshaping portion in a fourth embodiment of the guide wire.

Hereinafter, the fourth embodiment of the guide wire and a method for manufacturing the guide wire will be described while referring to FIG. 6. However, the description will mainly focus on differences between the fourth embodiment and the above-described embodiments, and the description of the same features will not be repeated.

The fourth embodiment is the same as the first embodiment except that the occupancy (i.e., volume) of a first material portion and a second material portion constituting the reshaping portion is different from that in the first embodiment.

The embodiment shown in FIG. 6 has a joint surface 33 that is deviated from the center $O_3$ of the reshaping portion 3 (i.e., biased to the right side of the drawing). Accordingly, the occupancy (i.e., volume) of the first material portion 31 becomes smaller than that of the second material portion 32. Therefore, for example, torque performance in the reshaping portion 3 is preferentially improved.

Fifth Embodiment

Figure 7:
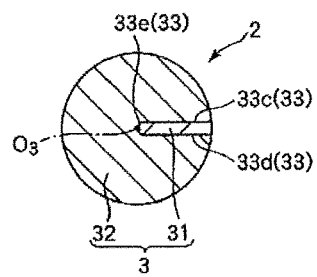
FIG. 7 is a transverse cross sectional view showing a reshaping portion in a guide wire (fifth embodiment).

FIG. 7 is a transverse cross sectional view showing a reshaping portion in a fifth embodiment of the guide wire.

Hereinafter, the fifth embodiment of the guide wire and a method for manufacturing the guide wire will be described while referring to this drawing. However, the description will focus on differences between the fifth embodiment and the above-described embodiments, and the description of the same features will not be repeated.

The fifth embodiment is the same as the first embodiment except that the occupancy (i.e., volume) of a first material portion and a second material portion constituting the reshaping portion is different from that in the first embodiment.

In the fifth embodiment shown in FIG. 7, the joint surfaces 33 includes joint surfaces 33c and 33d which are parallel to each other, and a curved joint surface 33e in contact with the center $O_3$ between the joint surface 33c and the joint surface 33d. All of the joint surfaces 33c to 33e follow (i.e., extend in) a longitudinal direction of the core wire 2. Accordingly, the occupancy (i.e., volume) of the first material portion 31 becomes smaller than that of the second material portion 32. Therefore, for example, flexibility in the reshaping portion 3 is preferentially improved. In addition, the present embodiment is effective when the first material portion 31 is as small as possible.

Sixth Embodiment

Figure 8:
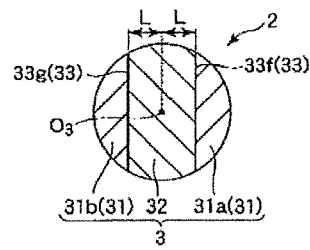
FIG. 8 is a transverse cross sectional view showing a reshaping portion in a guide wire (sixth embodiment).

FIG. 8 is a transverse cross sectional view showing a reshaping portion in a sixth embodiment of the guide wire.

Hereinafter, the sixth embodiment of the guide wire and a method for manufacturing the guide wire will be described while referring to this drawing. However, the description will focus on differences between the sixth embodiment and the above-described embodiments, and the description of the same features will not be repeated.

The sixth embodiment is the same as the first embodiment except that the arrangement of a first material portion and a second material portion constituting the reshaping portion is different from that in the first embodiment.

In the sixth embodiment shown in FIG. 8, the reshaping portion 3 is constituted of the two first material portions 31 (first material portions 31a and 31b) and the second material portion 32. The second material portion 32 is disposed between the one of the two first material portions 31a and the other of the two first material portions 31b. In this case, there are two joint surfaces 33—a joint surface 33f between one first material portion 31a and the second material portion 32, and a joint surface 33g between the other first material portion 31b and the second material portion 32. All of the joint surfaces 33f and 33g are deviated from the center $O_3$ by the same separation distance L. Accordingly, the ease of bending when, for example, the reshaping portion is bent to the right side in FIG. 8 is the same as the ease of bending when the reshaping portion is bent to the left side in FIG. 8. Therefore, operability during the reshaping is improved.

Note that the reshaping portion 3 is constituted of the two first material portions 31a, 31b and the second material portion 32 between the two first material portions 31a, 31b in the embodiment illustrated in FIG. 8. However, the reshaping portion 3 is not limited to this configuration, and the reshaping portion may be constituted of two second material portions 32 with the first material portion 31 between the two second material portions 32.

Seventh Embodiment

Figure 9:
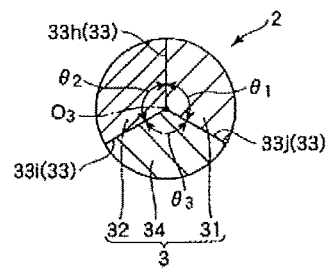
FIG. 9 is a transverse cross sectional view showing a reshaping portion in a guide wire (seventh embodiment).

FIG. 9 is a transverse cross sectional view showing a reshaping portion in a seventh embodiment of the guide wire.

Hereinafter, the seventh embodiment of the guide wire and a method for manufacturing the guide wire will be described while referring to this drawing. However, the description will mainly focus on differences between the seventh embodiment and the above-described embodiments, and the description of the same features will not be repeated.

The seventh embodiment is the same as the first embodiment except that the configuration of a reshaping portion is different from that in the first embodiment.

In this embodiment as shown in FIG. 9, the reshaping portion 3 includes a third material portion 34 which is disposed between the first material portion 31 and the second material portion 32 and is joined to each of the material portions 31, 32. There is a joint surface 33h between the first material portion 31 and the second material portion 32, a joint surface 33i between the second material portion 32 and the third material portion 34, and a joint surface 33j between the first material portion 31 and the third material portion 34 in this configuration. All of the joint surfaces 33h, 33i, 33j pass through the center $O_3$. Accordingly, the first material portion 31, the second material portion 32, and the third material portion 34 each possess fan shaped cross sectional shapes. By changing the occupancy (a portion of a central angle $\theta_1$) of the first material portion 31, the occupancy (a portion of a central angle $\theta_2$) of the second material portion 32, and the occupancy (a portion of a central angle $\theta_3$) of the third material portion 34, it is possible to produce a device (guide wire) which gives priorities to respective physical properties.

Note that the third material portion 34 is made of a third material which is different from a first material and a second material. The material of the third material portion 34 is not particularly limited. For example, it is possible to use β-Ti. β-Ti is a material which has comparatively higher biocompatibility than stainless steel or Ni—Ti based alloy.

When bending the reshaping portion 3 that possesses the above-described configuration, the ease of bending varies depending on the bending direction of the reshaping portion 3. When such physical properties are required for the reshaping portion 3, the configuration of the present embodiment is effective.

Eighth Embodiment

Figure 10:
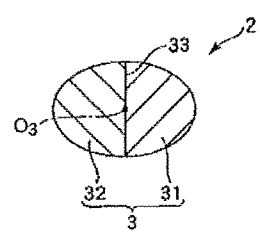
FIG. 10 is a transverse cross sectional view showing a reshaping portion in a guide wire (eighth embodiment).

FIG. 10 is a transverse cross sectional view showing a reshaping portion in an eighth embodiment of the guide wire.

Hereinafter, the eighth embodiment of the guide wire and a method for manufacturing the guide wire will be described while referring to this drawing. However, the description will mainly focus on differences between the eighth embodiment and the above-described embodiments, and the description of the same features will not be repeated.

The eighth embodiment is the same as the first embodiment except that the transverse cross sectional shape of a reshaping portion is different from that in the first embodiment.

As shown in the eighth embodiment illustrated in FIG. 10, the transverse cross sectional shape of the reshaping portion 3 is an elliptical shape. The joint surface 33 passes through the center $O_3$ of the elliptical shape in parallel to a minor diameter direction (i.e., the smaller outer diameter of the elliptical shape). In such a reshaping portion 3, the flexural rigidity becomes comparatively high.

Note that the joint surface 33 passes through the center $O_3$ in the embodiment illustrated in FIG. 10, but may instead be deviated from the center $O_3$.

The elliptical shape can be formed by selecting a mold 9 that has a cavity 93 equivalent to the shape (i.e., an elliptically shaped cavity).

Ninth Embodiment

Figure 11:
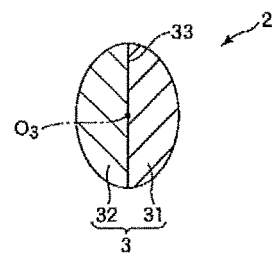
FIG. 11 is a transverse cross sectional view showing a reshaping portion in a guide wire (ninth embodiment).

FIG. 11 is a transverse cross sectional view showing a reshaping portion in a ninth embodiment of the guide wire.

Hereinafter, the ninth embodiment of the guide wire and a method for manufacturing the guide wire will be described while referring to this drawing. However, the description will mainly focus on differences between the ninth embodiment and the above-described embodiments, and the description of the same features will not be repeated.

The ninth embodiment is the same as the eighth embodiment except that the direction of the joint surface 33 is different from that in the eighth embodiment.

As shown in FIG. 11, the joint surface 33 of the ninth embodiment passes through the center $O_3$ of the elliptical shape in parallel to a major diameter direction (i.e., the larger outer diameter of the elliptical shape). In such a reshaping portion 3, the flexural rigidity is decreased compared to that of the reshaping portion in the eighth embodiment.

Tenth Embodiment

Figure 12:
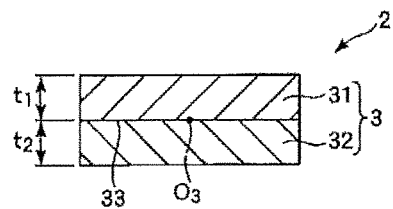
FIG. 12 is a transverse cross sectional view showing a reshaping portion in a guide wire (tenth embodiment).

FIG. 12 is a transverse cross sectional view showing a reshaping portion in a tenth embodiment of the guide wire.

Hereinafter, the tenth embodiment of the guide wire and a method for manufacturing the guide wire will be described while referring to this drawing. However, the description will mainly focus on differences between the tenth embodiment and the above-described embodiments, and the description of the same matters will not be repeated.

The tenth embodiment is the same as the eighth embodiment except that the transverse cross sectional shape of a reshaping portion is different from that in the eighth embodiment.

As shown in FIG. 12, the transverse cross sectional shape of the reshaping portion 3 of the tenth embodiment is a rectangle. The joint surface 33 passes through the center $O_3$ of the rectangle in parallel to a long side direction. In such a reshaping portion 3, the flexural rigidity is decreased compared to that of the reshaping portion in the eighth embodiment.

Note that the joint surface 33 passes through the center $O_3$ in the present embodiment, that is, the thickness $t_1$ of the first material portion 31 and the thickness $t_2$ of the second material portion 32 are the same as each other. However, the guide wire is not limited to a joint surface 33 that passes through the center $O_3$, and the joint surface 33 may be deviated (i.e., offset) from the center $O_3$, that is, the thickness $t_1$ and the thickness $t_2$ may be different from each other.

In addition, the thickness $t_1$ and the thickness $t_2$ are constant along a width direction (horizontal direction in the drawing) of the reshaping portion 3 in the present embodiment. However, the thickness is not limited a constant thickness, and the thickness $t_1$ and the thickness $t_2$ may change.

In addition, the thickness $t_1$ and the thickness $t_2$ may be constant or may change along a longitudinal direction (depth direction of paper in the drawing) of the reshaping portion 3.

The guide wire and the method for manufacturing the guide wire have been described based on the embodiments shown in the drawings. However, the guide wire and method for manufacturing the guide wire are not limited to the disclosed embodiments. In addition, each portion constituting the guide wire can be substituted with an arbitrary configuration which can exhibit the same function. In addition, an arbitrary component may be added thereto.

In addition, in the guide wire and the method for manufacturing the guide wire, two or more arbitrary structures (characteristics) in each of the embodiments may be combined with each other.

In each of the embodiments, the first material out of the first material and the second material is stainless steel and the second material is Ni—Ti based alloy. However, the materials are not limited to the disclosed materials, and the first material may be Ni—Ti based alloy and the second material may be stainless steel.

In each of the embodiments, the first material out of the first material and the second material is stainless steel and the second material is Ni—Ti based alloy. However, the materials are not limited to the disclosed materials, and the first material may be, for example, β-Ti.

INDUSTRIAL APPLICABILITY

The guide wire forms an elongated shape and includes a core wire having a reshaping portion, which can be reshaped, at a distal portion, in which the reshaping portion has at least a first material portion made of a first material, and a second material portion which is made of a second material different from the first material and is joined to the first material portion, and in which the joint surface between the first material portion and the second material portion follows a longitudinal direction of the core wire. For this reason, it is easy to perform reshaping at a distal portion of the guide wire, and the guide wire is excellent in torquability up to the distal portion.

The detailed description above describes a guide wire and a method of manufacturing the guide wire. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A guide wire comprising:
a core wire elongated in a longitudinal direction, the core wire possessing a proximal portion, a distal portion, and an outer diameter;
the distal portion of the core wire comprising a reshaping portion that is configured to be reshaped, the reshaping portion extending in the longitudinal direction of the core wire from a proximal-most end to a distal-most end, the distal-most end of the reshaping portion being a distal-most end of the core wire;
the reshaping portion comprising a first material portion made of a first material and a second material portion made of a second material different from the first material, the reshaping portion possessing an outer diameter;
the first material portion being joined to the second material portion at a joint surface which extends in the longitudinal direction of the core wire, the first material portion and the second material portion extending along the entirety of the reshaping portion in the longitudinal direction from the distal-most end of the reshaping portion to the proximal-most end of the reshaping portion such that the joint surface also extends for the entirety of the reshaping portion in the longitudinal direction;
the core wire comprising a main body portion positioned proximal to the reshaping portion, the main body portion comprising a back end portion and a tapered portion between the back end portion and the reshaping portion in the longitudinal direction, the main body portion possessing an outer diameter, the tapered portion extending for a length in the longitudinal direction with the outer diameter of the tapered portion varying along the length in the longitudinal direction, the tapered portion possessing a distal end and a proximal end, the proximal end of the tapered portion possessing an outer diameter equal to the outer diameter of the back end portion, the distal end of the tapered portion being connected to the proximal-most end of the reshaping portion and possessing an outer diameter equal to the outer diameter of the reshaping portion, the outer diameter of the back end portion being greater than the outer diameter of the reshaping portion; and
the main body portion and tapered portion being formed from the first material, and all of the second material being entirely distal to the tapered portion of the main body portion of the core wire.

2. The guide wire according to claim 1, wherein the reshaping portion possesses a transverse cross sectional shape that is a circular shape or an elliptical shape.

3. The guide wire according to claim 2, wherein the joint surface is spaced apart from a center of the circular shape or the elliptical shape.

4. The guide wire according to claim 2,
wherein the first material portion and the second material portion each possess a fan-shaped transverse cross sectional shape, and
wherein a central angle of the first material portion and a central angle of the second material portion are different from each other.

5. The guide wire according to claim 2, wherein
the reshaping portion comprises a third material portion, the third material portion being made of the first material;
the third material portion is joined to the second material portion at a second joint surface which extends in the longitudinal direction of the core wire; and
the second material portion is positioned between the first material portion and the third material portion.

6. The guide wire according to claim 1, wherein the back end portion and the tapered portion of the main body portion is formed integrally with the first material portion which is the same constituent material as that of the back end portion and the tapered portion of the main body portion.

7. The guide wire according to claim 6, wherein the first material portion which is the same constituent material as the main body portion has a large cross-sectional area ratio in the cross-section of the reshaping portion.

8. The guide wire according to claim 1, wherein one of the first material and the second material is stainless steel and an other of the first material and the second material is Ni—Ti based alloy.

9. The guide wire according to claim 1, wherein the reshaping portion comprises a third material portion which is made of a third material different from the first material and the second material, the third material portion being joined to the first material portion and the second material portion between the first material portion and the second material portion.

10. The guide wire according to claim 9, wherein one of the first material and the second material is stainless steel and an other is Ni—Ti based alloy, and the third material is β-Ti.

11. A guide wire comprising:
a main body extending in a longitudinal direction, the main body possessing a distal-most end;
a tapered portion possessing a proximal end and a distal end, the proximal end of the tapered portion being connected to the distal-most end of the main body;

a first extension portion possessing a proximal end and a distal end, the proximal end of the first extension portion being directly connected to the distal end of the tapered portion;

the main body, the tapered portion, and the first extension portion being integrally formed at one time as a unitary structure from a first material;

a second extension portion made from a second material different from the first material, the second extension portion being joined to the first extension portion at a joint surface extending in the longitudinal direction, the entirety of the second material terminates at a proximal end that is joined to the distal end of the tapered portion;

the first extension portion and the second extension portion collectively defining a reshaping portion of the guide wire, the reshaping portion possessing an outer surface; and the first material forming part of the outer surface of the reshaping portion and the second material forming an other part of the outer surface of the reshaping portion, the part of the outer surface of the reshaping portion and the other part of the outer surface of the reshaping portion overlapping one another in the longitudinal direction, wherein the first extension portion possesses a length in the longitudinal direction between the distal and proximal ends of the first extension portion, and the second extension portion extends for the entirety of the length of the first extension portion in the longitudinal direction such that a length of the second extension portion equals the length of the first extension portion.

12. The guide wire according to claim 11, further comprising a coil extending in the longitudinal direction, the coil possessing an inner surface and surrounding the reshaping portion such that the inner surface of the coil faces the outer surface of the reshaping portion.

13. The guide wire according to claim 12, wherein the inner surface of the coil is spaced apart from the outer surface of the reshaping portion.

14. The guide wire according to claim 12, wherein
the coil possesses a proximal end and a distal end; and
the proximal end of the coil is fixed to the tapered portion of the guide wire and the distal end of the coil is fixed to a distal end of the reshaping portion.

15. The guide wire according to claim 11, wherein the reshaping portion is cylindrically shaped, and the first extension portion and the second extension portion each form one half of the cylindrical shape of the reshaping portion.

16. The guide wire according to claim 1, wherein the outer diameter of the reshaping portion is continuous along the entirety of the reshaping portion in the longitudinal direction.

17. The guide wire according to claim 16, wherein
the reshaping portion possesses an outer circumferential area, and
the first and second material portions each possess an outer circumferential area that is one half the outer circumferential area of the reshaping portion.

18. The guide wire according to claim 1, wherein the second material portion is a half-cylindrically shaped body with a constant half-cylindrical shape throughout the entirety of the second material portion.

19. The guide wire according to claim 1, wherein the outer diameter of the back end portion is constant throughout the entirety of the back end portion in the longitudinal direction.

20. The guide wire according to claim 11, wherein the reshaping portion possesses an outer diameter that is continuous along the entirety of the reshaping portion in the longitudinal direction.

21. The guide wire according to claim 20, wherein
the reshaping portion possesses an outer circumferential area, and
the first and second extension portions each possess an outer circumferential area that is one half the outer circumferential area of the reshaping portion.

22. The guide wire according to claim 11, wherein the second extension portion is a half-cylindrically shaped body with a constant half-cylindrical shape throughout the entirety of the second extension portion.

23. The guide wire according to claim 11, wherein the outer diameter of the main body is constant throughout the entirety of the main body in the longitudinal direction.

* * * * *